United States Patent [19]

Klosek et al.

[11] 4,379,027

[45] Apr. 5, 1983

[54] SELECTIVE HYDROGENATION OF VINYLTOLUENE

[75] Inventors: John M. Klosek, Sewaren; Margaret M. Wu, Belle Mead, both of N.J.

[73] Assignee: Mobil Oil Corporation, New York, N.Y.

[21] Appl. No.: 334,346

[22] Filed: Dec. 24, 1981

[51] Int. Cl.$^3$ .......................... B01D 3/14; C07C 5/10; C07C 7/04; C07C 7/163
[52] U.S. Cl. .................................. 203/32; 252/455 Z; 423/328; 585/258; 585/267; 585/269; 585/270; 585/806; 585/807
[58] Field of Search .................................. 203/32, 99; 585/266–270; 585/807, 804; 423/328, 327, 329; 252/455 Z, 459, 460

[56] References Cited

U.S. PATENT DOCUMENTS

| | | | |
|---|---|---|---|
| 3,684,665 | 8/1972 | Abe et al. | 203/32 |
| 3,702,886 | 11/1972 | Argauer et al. | 423/328 |
| 3,709,979 | 1/1973 | Chu | 423/328 |
| 3,715,408 | 2/1973 | Brown et al. | 203/32 |
| 3,943,053 | 3/1976 | Kovach et al. | 585/266 |
| 4,046,824 | 9/1977 | Ransley | 585/266 |
| 4,075,254 | 2/1978 | Boodman et al. | 585/258 |
| 4,299,686 | 11/1981 | Kuehl | 585/258 |
| 4,341,600 | 7/1982 | Watson | 203/9 |

*Primary Examiner*—Wilbur L. Bascomb, Jr.
*Attorney, Agent, or Firm*—Charles A. Huggett; Michael G. Gilman; Edward J. Trojnar

[57] ABSTRACT

This invention provides a process for obtaining m-methylstyrene from a mixture with p-methylstyrene that comprises hydrogenating a mixture of p-methylstyrene and m-methylstyrene in the presence of a zeolite having a Constraint Index of about 1 to about 12, a silica to alumina mole ratio of at least about 12, and a dried crystal density of not less than about 1.6 grams per cubic centimeter, modified with at least one element of Group IA, IIA, IVB, or VB of the Periodic Chart of the Elements and a metal of Group VIII of the Periodic Chart of the Elements; thereby obtaining a mixture of m-methylstyrene and p-ethyltoluene, and removing p-ethyltoluene by distillation.

9 Claims, No Drawings

SELECTIVE HYDROGENATION OF VINYLTOLUENE

BACKGROUND OF THE INVENTION

1. Field of the Invention

This invention is concerned with selective hydrogenation of vinyltoluene to prepare polymer grade m-methylstyrene.

2. Description of the Prior Art

Insofar as is now known, it has not been proposed to use a modified zeolite to selectively hydrogenate vinyltoluene.

SUMMARY OF THE INVENTION

This invention provides a process for obtaining m-methylstyrene from a mixture with p-methylstyrene that comprises hydrogenating a mixture of p-methylstyrene and m-methylstyrene in the presence of a zeolite having a Constraint Index of about 1 to about 12, a silica to alumina mole ratio of at least about 12, and a dried crystal density of not less than about 1.6 grams per cubic centimeter, modified with at least one element of Group IA, IIA, IVB, or VB of the Periodic Chart of the Elements and a metal of Group VIII of the Periodic Chart of the Elements; thereby obtaining a mixture of m-methylstyrene and p-ethyltoluene, and removing p-ethyltoluene by distillation.

DESCRIPTION OF SPECIFIC EMBODIMENTS

The feed to the process of this invention is a mixture of p-methylstyrene and m-methylstyrene, such as vinyltoluene. Vinyltoluene has been commercially available for quite a long time. In general, it is a mixture of about 30–50 weight percent para isomer and about 50–70 weight percent meta isomer. In many polymer applications, this mixture of monomers is not satisfactory. Substantially pure meta or para isomer is more desirable.

In the process of this invention, vinyltoluene is selectively catalytically hydrogenated to reduce only the para isomer to p-ethyltoluene. The catalyst used is a zeolite having a Constraint Index of about 1 to about 12, a silica to alumina mole ratio of at least about 12, and a dried crystal density of not less than about 1.6 grams per cubic centimeter, modified with at least one element of Group IA, IIA, IVB, or VB of the Periodic Chart of the Elements and with a metal of Group VIII of the Periodic Chart of the Elements. The Periodic Chart of the Elements referred to is published by the Fisher Scientific Company, Cat. No. 5-702-10. It is accepted by the International Union for Pure and Applied Chemistry and has been checked by the National Bureau of Standards' Office of Standard Reference Data. Non-limiting examples of elements of Groups IA, IIA, IVB, and VB include Na, K, Cs, Mg, Si, and P. Non-limiting examples of Group VIII elements include Pt, Pd, Ni, Co, and Rh.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conductive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48, and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

$(0-15)RN: (0-1.5)M_{2/n}O: (0.2)Al_2O_3: (100)SiO_2$ wherein:

M is at least one cation having a valence n; and

RN is a $C_1$–$C_{20}$ organic compound having at least one amine functional group of $pK_a \geq 7$.

It is recognized that, particularly when the composition contains tetrahedral framework aluminum, a fraction of the amine functional groups may be protonated. The doubly protonated form, in conventional notation, would be $(RNH)_2O$ and is equivalent in stoichiemetry to $2\,RN + H_2O$.

The characteristic X-ray diffraction pattern of the synthetic zeolite ZSM-48 has the following significant lines:

| Characteristic Lines of ZSM-48 | |
| --- | --- |
| d (Angstroms) | Relative Intensity |
| 11.9 | W–S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100\,I/I_o$, where $I_o$ is the intensity of the strongest line or peak, and d (obs.), the interplanar spacing in angstroms, corresponding to the recorded lines, were calculated. In the foregoing table the relative intensities are given in terms of the symbols W=weak, VS=very strong and W-S=weak-to-strong. Ion exchange of the sodium ion with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

| REACTANTS | | BROAD | PREFERRED |
| --- | --- | --- | --- |
| $Al_2O_3/SiO_2$ | = | 0 to 0.02 | 0 to 0.01 |
| $Na/SiO_2$ | = | 0 to 2 | 0.1 to 1.0 |
| $RN/SiO_2$ | = | 0.01 to 2.0 | 0.05 to 1.0 |
| $OH^-/SiO_2$ | = | 0 to 0.25 | 0 to 0.1 |
| $H_2O/SiO_2$ | = | 10 to 100 | 20 to 70 |
| $H^+$ (added) $SiO_2$ | = | 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor, at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pk_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by calcination and/or ion exchange with another cation. Thus, the original cations are exchanged into a hydrogen or hydrogen ion precursor form or a form in which the original cation has been replaced by a metal of Groups II through VIII of the Periodic Table. Thus, for example, it is contemplated to exchange the original cations with ammonium ions or with hydronium ions. Catalytically active forms of these would include, in particular, hydrogen, rare earth metals, aluminum, manganese and other metals of Groups II and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

The crystalline zeolites employed are modified prior to use by combining therewith a small amount, generally in the range of about 0.5 to about 40 weight percent, of a difficultly reducible oxide, such as the oxides of sodium, potassium, phosphorus, boron, magnesium or combinations thereof and also oxides of antimony. Modification of the zeolite with the desired oxide or oxides can readily be effected by contacting the zeolite with a solution of an appropriate compound of the element to be introduced, followed by drying and calcining to convert the compound to its oxide form.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P=O$, $R_3P=S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)OX$, phosphonic acids such as benzene phosphonic acid; the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphonates, $(RO)P(O)R_2$; phosphinous acids, $R_2POX$, such as diethylphosphinous acid, primary, $(RO)P(OX)_2$, secondary, $(RO)_2POX$, and tertiary $(RO)$ P, phosphites and esters thereof such as the monopropyl ester, alkyl dialkylphosphinites, $(RO)PR_2$, and dialkyl alkylphosphonite, $(RO)_2PR$, esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PCl$, dialkylphosphinochloridites, $R_2PCl$, alkyl alkylphosphonochloridates, $(RO)(R)P(O)Cl$, dialkyl phosphinochloridates, $R_2P(O)Cl$ and $RP(O)Cl_2$. Applicable corresponding sulfur derivatives include $(RS)PCl_2$, $(RS)_2PCl$, $(RS)(R)P(S)Cl$ and $R_2P(S)Cl$.

Preferred phosphorus-containing compounds include dibasic ammonium phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate and other alcohol-$P_2O_5$ reaction products.

Reaction of the zeolite with the phosphorus compound is effected by contacting the zeolite with such compound. Where the treating phosphorus compound is a liquid or a solid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the phosphorus-containing compound is, for example, trimethylphosphite or liquid phosphorus trichloride, a hydrocarbon solvent such as octane may be employed. The liquid phosphorus-containing compound may be used without a solvent, i.e., as a neat liquid. Where the phosphorus-containing compound is in the gaseous phase, such as where gaseous phosphorus trichloride is employed, the treating compound can be used by itself or can be used in admixture with a gaseous diluent relatively inert to the phosphorus-containing compound and the zeolite, such as air or nitrogen, or with an organic solvent, such as octane or toluene.

Prior to reacting the zeolite with the phosphorus-containing compound, the zeolite may be dried. Drying can be effected in the presence of air. Elevated temperatures may be employed. However, the temperature should not be such that the crystal structure of the zeolite is destroyed.

Heating of the phosphorus-containing catalyst subsequent to preparation and prior to use is also preferred. The heating can be carried out in the presence of oxygen—for example, in air. Heating can be at a temperature of about 150° C. However, higher temperatures, e.g., up to about 500° C., are preferred. Heating is generally carried out for 3–5 hours but may be extended to 24 hours or longer. While heating temperatures above about 500° C. can be employed, they are generally not necessary. At temperatures of about 1000° C. the crystal structure of the zeolite tends to deteriorate.

The amount of phosphorus incorporated with the zeolite should be at least about 0.25 percent by weight. However, it is preferred that the amount of phosphorus in the zeolite be at least about 1 percent by weight when the same is combined with a binder, e.g. 35 weight percent of alumina. The amount of phosphorus can be as high as about 25 percent by weight or more depending on the amount and type of binder present. Preferably, the amount of phosphorus added to the zeolite is between about 0.5 and about 15 percent by weight.

The amount of phosphorus incorporated with the zeolite by reaction with elemental phosphorus or phosphorus-containing compound will depend upon several factors. One of these is the reaction time, i.e., the time that the zeolite and the phosphorus-containing source are maintained in contact with each other. With greater reaction times, all other factors being equal, a greater amount of phosphorus is incorporated with the zeolite. Other factors upon which the amount of phosphorus incorporated with the zeolite is dependent include reaction temperature, concentration of the treating compound in the reaction mixture, the degree to which the zeolite has been dried prior to reaction with the phosphorus-containing compound, the conditions of drying of the zeolite after reaction with the treating compound, and the amount and type of binder incorporated with the zeolite.

Another suitable modifying oxide is that of magnesium. Representative magnesium-containing compounds include magnesium acetate, magnesium nitrate, magnesium benzoate, magnesium propionate, magnesium 2-ethylhexoate, magnesium carbonate, magnesium formate, magnesium oxylate, magnesium amide, magnesium bromide, magnesium hydride, magnesium lactate, magnesium laurate, magnesium oleate, magnesium palmitate, magnesium salicylate, magnesium stearate and magnesium sulfide.

Reaction of the zeolite with the treating magnesium compound is effected by contacting the zeolite with such compound. Where the treating compound is a liquid or solid, such compound can be in solution in a solvent at the time contact with the zeolite is effected. Any solvent relatively inert with respect to the treating magnesium compound and the zeolite may be employed. Suitable solvents include water and aliphatic, aromatic or alcoholic liquid. The treating compound may also be used without a solvent, i.e. as a neat liquid. Where the treating compound is in the gaseous phase, it can be used by itself or in admixture with a gaseous diluent relatively inert to the treating compound and the zeolite such as helium or nitrogen, or with an organic solvent such as octane or toluene.

Heating of the magnesium compound impregnated catalyst subsequent to preparation and prior to use is preferred. The heating can be carried out in the presence of oxygen—for example, in air. Heating can be at a temperature of about 150° C. However, higher temperatures, e.g. up to about 500° C., are preferred. Heating is generally carried out for 1-5 hours but may be extended to 24 hours or longer. While heating temperatures above about 500° C. may be employed, they are generally not necessary. At temperatures of about 1000° C. the crystal structure of the zeolite tends to deteriorate. After heating in air at elevated temperatures, the oxide form of magnesium is present.

The amount of magnesium oxide incorporated in the zeolite should be at least about 0.25 percent by weight. However, it is preferred that the amount of magnesium oxide in the zeolite be at least about 1 percent by weight, particularly when the same is combined with a binder, e.g. 35 weight percent of alumina. The amount of magnesium oxide can be as high as about 25 percent by weight or more depending on the amount and type of binder present. Preferably, the amount of magnesium oxide added to the zeolite is between about 0.5 and about 15 percent by weight.

Boron oxide is also an effective modifying component. Representative boron-containing compounds include boric acid, trimethylborate, boron hydride, boron oxide, boron sulfide, butylboron dimethoxide, butylboronic acid, dimethylboric anhydride, hexamethylborazine, phenylboric acid, triethylborane, tetramethylammonium borohydride, triphenyl boron, and allylborate.

Reaction of the zeolite with the boron compound is effected by contacting the zeolite with such compound. Where the treating boron compound is a liquid, such compound can be in solution in a solvent at the time contact with the zeolite is effected. Any solvent relatively inert with respect to the treating compound and the zeolite may be employed. Suitable solvents include water and aliphatic, aromatic or alcoholic liquids. Where the boron containing compound is, for example, trimethylborate, a hydrocarbon solvent such as octane may be employed. The boron-containing compound may be used without a solvent, i.e., may be used as a neat liquid. Where the boron-containing compound is in the gaseous phase, such as where gaseous diborane is employed, the treating compound can be used by itself or can be used in admixture with a gaseous diluent inert to the boron-containing compound and the zeolite, such as nitrogen or helium, or with an organic solvent, such as octane.

Prior to reacting the zeolite with the boron-containing compound, the zeolite may be dried. Drying can be effected in the presence of air. Elevated temperatures may be employed. However, the temperature should not be such that the crystal structure of the zeolite is destroyed.

Heating of the boron-containing catalyst subsequent to preparation and prior to use is also preferred. The heating can be carried out in the presence of oxygen, for example, air. Heating can be at a temperature of about 150° C. However, higher temperatures, e.g., up to about 500° C., are preferred. Heating is generally carried out for 3-5 hours but may be extended to 24 hours or longer. While heating temperatures above about 500° C. can be employed, they are generally not necessary. At temperatures of about 1000° C. the crystal structure of the zeolite tends to deteriorate.

The amount of boron incorporated with the zeolite should be at least about 0.25 percent by weight. However, it is preferred that the amount of boron in the zeolite be at least about 1 percent by weight when the same is combined with a binder, e.g. 35 weight percent of alumina. The amount of boron can be as high as about 20 percent by weight or more depending on the amount and type of binder present. Preferably, the amount of boron added to the zeolite is between about 1.5 and 10 percent by weight. Without being limited by any theoretical considerations, it is contemplated that boron is actually present in the zeolite in an oxidized state, such as $B_2O_3$.

Antimony oxide may also be employed as a modifying component. The antimony oxide is present as $Sb_2O_3$ alone or in admixture with other antimony oxides with or without metallic antimony or other antimony compounds being present. In all instances, regardless of the particular state of oxidation of the antimony, its content with respect to the zeolite is computed as if it were present as $Sb_2O_3$. Generally the amount of $Sb_2O_3$ in the composite catalyst will be between about 6 and about 40 weight percent and preferably between about 10 and about 35 weight percent. Antimony derivatives which may be used include: the hydride $SbH_3$; the halides $SbX_3$, $SbX_5$ (X=F, Cl, Br, I); organic alkyl and aryl stibines and their oxides $R_3Sb$, $R_5Sb$, $R_xSb=O$ (R=alkyl or aryl); halogen derivatives $RSbX_2$, $R_2SbX$, $RSbX_4$, $R_2SbX_3$, $R_3SbX_2$, $R_4SbX$; the acids $H_3SbO_3$, $HSbO_2$, $HSb(OH)_6$; organic acids such as $RSbO(OH)_2$, $R_2SbO \cdot OH$, all with R and X defined as above noted. Also included are organic ethers such as $R_2SbOSbR_2$; esters and alcoholates such as $Sb(OOCCH_3)_3$, $Sb(OC_4H_9)_3$, $Sb(OC_2H_5)_3$, $Sb(OCH_3)_3$; and anitmony salts as $(SbO)SO_4$, $(SbO)NO_3$, $K(SbO)C_4H_4O_6$, $NaSbO_2\cdot 3H_2O$.

In some instances, it may be desirable to modify the crystalline aluminosilicate zeolite by combining therewith two or more of the specified oxides. Thus, the zeolite may be modified by prior combination therewith of oxides of phosphorus and boron, oxides of phosphorus and magnesium or oxides of magnesium and boron. When such modification technique is employed, the oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between 0.5 and about 40 weight percent.

The zeolite catalyst is also modified with a Group VIII metal by soaking it in a solution, usually aqueous, of a suitable compound containing the desired Group VIII metal. The compound can be any compound usually used in catalyst manufacture, preferably one in which the components other than the Group VIII metal will be driven off when heated to dry or calcine. Suitable compounds include metal chlorides, nitrates, acetates, and the ammine complexes. Typical techniques for preparing the catalysts used in the process of this invention are demonstrated in the examples. Preferably, the Group VIII metal is put onto the zeolite first. The amount of Group VII metal on the zeolite should be 0.005–1.0 wt. %, preferably 0.01–0.1 wt. %.

The process of this invention requires the presence of a molecular hydrogen containing gas, which can be hydrogen or a gas mixture containing hydrogen. A suitable gas mixture is syngas, which is a mixture of hydrogen and carbon monoxide of a molar ratio of about 0.5–3 hydrogen to 1–20 carbon monoxide, preferably 1–10. The amount of hydrogen should be sufficient to hydrogenate the p-methylstyrene, i.e., at least a stoichiometric amount. Preferably, an excess of the stoichiometric amount is used.

In the examples and claims, an abbreviation has been used to designate the catalyst by reciting the modifying elements followed by the form and type zeolite used. Thus, Na, Pt-ZSM-5 designates ZSM-5 modified with sodium and platinum.

The hydrogen feed rate will be between about 0.05 and about 0.15 WHSV (weight hourly space velocity). The vinyltoluene feed rate will be between about 0.1 and about 50 WHSV. The temperature of hydrogenation is between about 150° C. about 500° C.

The hydrogenation is selective and produces a product consisting essentially of m-methylstyrene and p-ethyltoluene. The latter is readily separated and removed by simple distillation. The p-ethyltoluene can be steam dehydrogenated to p-methylstyrene, using well known self-regenerated dehydrogenation catalysts. Poly-(p-methylstyrene) can be thermoformed to shaped containers that are crosslinked by ionizing radiation to become resistant to fats under microwave oven conditions, as is disclosed in U.S. Pat. No. 4,205,114, incorporated herein by reference. The m-methylstyrene can be used to form polymers useful for films and molded articles in applications used for polystyrene.

EXAMPLE 1

A 5.0 g portion of hydrogen form ZSM-5 of 14–20 mesh was added to a solution of tetrammine platinum (II) chloride dissolved in 100 cc. distilled water and let stand at room temperature for one hour. The catalyst was filtered, washed with 100 cc. distilled water four times, and dried at 100° C. The dried catalyst was further exchanged with 100 cc. of 1% aqueous sodium carbonate at room temperature for 2 hours. This catalyst was then filtered, washed with 100 cc. distilled water four times, and dried at 110° C. for 16 hours to give Na, Pt-ZSM-5.

Two grams of the dried catalyst was packed into a quartz microreactor. The catalyst was tested for selective hydrogenation by passing a commercial mixture of vinyltoluene (VT) containing about 63 wt. % meta- and about 37 wt. % para-isomers and hydrogen through the catalyst. Feed rate, reaction conditions, and results are set forth in Table I.

EXAMPLE 2

A 2 g. portion of the catalyst prepared as described in Example 1 was added to an aqueous solution of 10% $(NH_4)_2HPO_4$ and let stand for one hour at room temperature. The catalyst was then filtered, washed with 100 cc. deionized water twice, dried, and calcined at 500° C. in air. The resulting catalyst, P, Na, Pt-ZSM-5, was tested for selective hydrogenation as in Example 1. Feed rate, reaction conditions, and results are set forth in Table I.

EXAMPLE 3

Hydrogen form ZSM-5 zeolite was added to an aqueous solution of 10% $(NH_4)_2\ HPO_4$ and let stand for one hour at room temperature. The catalyst was then filtered, washed with 100 cc. deionized water twice, dried, and calcined at 500° C. in air. A 5 g. portion of the catalyst was added to a solution of 0.0042 g. tetrammine platinum (II) chloride in 100 cc. water and let stand at room temperature for one hour. The catalyst was then filtered, washed with 100 cc. deionized water four times, and dried at 100° C. Two grams of the resulting catalyst, Pt, P-ZSM-5, was tested for selective hydrogenation as in Example 1. Feed rate, reaction conditions, and results are set forth in Table 1.

EXAMPLE 4

A catalyst was prepared in a manner like that described in Example 1, except that instead of platinum tetrammine chloride there was used a solution of 0.0031 g. diammine palladium (II) chloride in 100 cc. deionized water. Two grams of the resulting catalyst, Na, Pd-ZSM-5, was tested for selective hydrogenation as in Example 1. Feed rate, reaction conditions, and results are set forth in Table I.

EXAMPLE 5

A 2.0 g. portion of ammonium form ZSM-5. (70/1 $SiO_2/Al_2O_3$ molar ratio) was added to a solution 0.0083 g. tetrammine palladium (II) chloride in 10 cc. hot deionized water and let stand for 16 hours at 50° C. The catalyst was filtered, washed with 50 cc. water four times and dried. Then the catalyst was washed with 10 cc. of 10% aqueous $Na_2CO_3$, 50 cc. deionized water four times and dried. The resulting catalyst, Na, Pd-ZSM-5, was tested for selective hydrogenation as in Example 1. Feed rate, reaction conditions, and results are set forth in Table I.

EXAMPLE 6

A catalyst was prepared in a manner like that described in Example 5, except that instead of tetrammine palladium (II) chloride there was used a solution of 0.0091 g. hexammine rhodium (III) chloride in 10 cc. water. The resulting catalyst, Na, Rh-ZSM-5 was tested for selective hydrogenation as in Example 1. Feed rate, reaction conditions, and results are set forth in Table I.

EXAMPLE 7

A catalyst was prepared in a manner like that described in Example 5, except that instead of tetrammine palladium (II) chloride there was used a solution of 0.0172 g. nickel nitrate in 10 cc. hot water. The resulting catalyst, Na, Ni-ZSM-5, was tested for selective hydrogenation as in Example 1. Feed rate, reaction conditions, and results are set forth in Table I.

For purposes of brevity, abbreviations have been used in the tables. These abbreviations are:

| | |
|---|---|
| VT | Vinyl toluene (feed) |
| PET | p-ethyltoluene |
| MET | m-ethyltoluene |
| PMS | p-methylstyrene |
| MMS | m-methylstyrene |
| MS | methylstyrene |
| Cp | conversion of PMS |
| Cm | conversion of MMS |

TABLE I

| Catalyst | 1 | 2 | 3 | 4 | 5 | 6 | 7 |
|---|---|---|---|---|---|---|---|
| Zeolite | ZSM-5[1] | ZSM-5[1] | ZSM-5[1] | ZSM-5[1] | ZSM-5[2] | ZSM-5[2] | ZSM-5[2] |
| Modifier | Na,Pt | P,Na,Pt | Pt,P | Na,Pd | Na,Pd | Na,Rh | Na,Ni |
| Amt | 2g. | 2g. | 2g. | 4g. | 2g. | 2g. | 2g. |
| Temp., °C. | 400 | 150 | 300 | 400 | 310 | 320 | 500 |
| VT, cc./hr. | 2.6 | 3.4 | 3.4 | 5.1 | 8.0 | 3.1 | 1.5 |
| H$_2$, cc./min. | 80 | 200 | 200 | 40 | 20 | 60 | 60 |
| Conv. of VT | 50.6 | 22.6 | 44 | 50 | 6.5 | 18.0 | 4.9 |
| Product Distribution (Wt. %) | | | | | | | |
| PET | 22.7 | 7.3 | 14.8 | 25.1 | 4.0 | 12.3 | 2.0 |
| MET | 22.3 | 14.4 | 15.2 | 24.5 | 2.7 | 4.8 | 2.0 |
| PMS | 9.6 | 15.6 | 8.4 | 9.7 | 26.6 | 18.7 | 29.2 |
| MMS | 39.8 | 61.7 | 47.5 | 39.8 | 66.7 | 63.2 | 65.9 |
| Others | 0.6 | 0.9 | 14.1 | 0.9 | 0 | 0 | 0 |
| MS in Product | 49.4 | 77.4 | 56.0 | 49.5 | 93.4 | 81.9 | 95.0 |
| % Para-MS | 19.4 | 20.2 | 15.1 | 19.6 | 28.5 | 22.9 | 30.7 |
| % Meta-MS | 80.6 | 79.8 | 84.9 | 80.4 | 71.5 | 77.1 | 69.3 |
| % Conv. of | | | | | | | |
| PMS (Cp) | 69.1 | 56.4 | 76.5 | 74.4 | 16.6 | 41.4 | 8.5 |
| MMS (Cm) | 42.2 | 3.9 | 26.0 | 35.4 | 1.9 | 7.1 | 3.1 |
| Cp/Cm | 1.6 | 14.5 | 2.9 | 2.1 | 8.7 | 5.8 | 2.7 |

[1] Crystal size 0.2–0.5 microns
[2] Crystal size greater than 1 micron

EXAMPLE 8

A 2.5 g. portion of ammonium form ZSM-5 (70/1 SiO$_2$/Al$_2$O$_3$) was added to a solution of 0.0061 g. tetrammine platinum (II) chloride in 10 cc. hot deionized water and let stand at 50° C. for 16 hours. The catalyst was filtered, washed with 50 cc. water four times, and dried. The dried catalyst was then exchanged with 10 cc. aqueous 10% Na$_2$CO$_3$ solution, washed, and dried. The catalyst, Na, Pt-ZSM-5, was tested for selective hydrogenation in a continuous operation. During this operation, temperature was varied in a range between about 300° C. and about 335° C. The feed rate of vinyltoluene was varied between about 8.4 cc./hr. and about 3.4 cc./hr. Hydrogen feed rate was maintained at about 40 cc./min. throughout. Pertinent data for the operation through 53.5 hours are set forth in Table II.

EXAMPLE 9

The catalyst used in Example 8, still in the reactor, was regenerated by calcining at 500° C. with a stream of air and nitrogen for half an hour. The calcined catalyst was tested for selective hydrogenation in the continuous operation. Pertinent data for the operation from 53.5 hours through 103.25 hours are set forth in Table III.

TABLE III

EXAMPLE 9, calcined Na, Pt-ZSM-5

| Run No. | 12 | 13 | 14 | 15 | 16 | 17 |
|---|---|---|---|---|---|---|
| Temp., °C. | 335 | → | → | 395 | 335 | 335 |
| Feed Rate | | | | | | |
| VT, cc./hr. | 3.4 | → | → | → | → | → |
| H$_2$, cc./min. | 60 | → | → | → | → | → |
| Time on Stream (hrs.) | 53.75 | 61.75 | 75.75 | 80.75 | 89.75 | 103.25 |
| % Conv. of VT | 45.2 | 38.4 | 33.2 | 36.2 | 32.7 | 27.6 |

TABLE II

EXAMPLE 8
Catalyst, 2g, Na, Pt-ZSM-5[1](70/1 SiO$_2$/Al$_2$O$_3$)

| Run No. | VT | 1 | 2 | 3 | 4 | 5 | 6 | 7 | 8 | 9 | 10 | 11 |
|---|---|---|---|---|---|---|---|---|---|---|---|---|
| Temp., °C. | — | 300 | → | 320 | → | → | → | → | → | 335 | → | 335 |
| Feed Rate | | | | | | | | | | | | |
| VT, cc./hr. | — | 8.4 | → | → | 5.1 | 3.4 | → | → | → | → | → | 3.4 |
| H$_2$, cc./min. | — | 40 | → | → | → | → | → | → | → | → | → | 40 |
| Time on Stream (hrs.) | 0 | 1 | 1.75 | 2.25 | 2.75 | 4.5 | 5.5 | 22 | 31 | 32 | 39.25 | 53.5 |
| % Conv. of VT | — | 39.1 | 34.8 | 35.1 | 40.6 | 54.0 | 54.9 | 48.2 | 43.3 | 34.1 | 34.0 | 21.5 |
| Product Distri- (wt. %) | | | | | | | | | | | | |
| PET | 0 | 27.2 | 26.2 | 27.0 | 28.1 | 30.9 | 30.9 | 29.6 | 31.6 | 31.7 | 31.9 | 5.8 |
| MET | 0 | 11.5 | 8.7 | 8.0 | 12.5 | 23.0 | 23.9 | 18.5 | 11.1 | 1.6 | 1.5 | 5.3 |
| PMS | 36.6 | 7.7 | 10.1 | 8.0 | 4.6 | 1.0 | 0.8 | 2.2 | 0.5 | 1.4 | 0.8 | 23.0 |
| MMS | 62.7 | 52.5 | 54.4 | 56.1 | 54.1 | 44.3 | 43.5 | 48.9 | 55.5 | 63.8 | 64.5 | 54.8 |
| Others | 0.7 | 1.0 | 0.6 | 0.7 | 0.7 | 0.8 | 0.8 | 0.8 | 1.3 | 1.5 | 1.3 | 11.1 |
| % MS in Product | 99.3 | 60.2 | 64.5 | 64.2 | 58.7 | 45.3 | 44.4 | 51.1 | 56.0 | 65.2 | 65.3 | 77.8 |
| % para | 36.8 | 12.9 | 15.6 | 12.5 | 7.9 | 2.2 | 1.9 | 4.3 | 0.9 | 2.2 | 1.2 | 29.5 |
| % meta | 63.2 | 87.1 | 84.4 | 87.5 | 92.1 | 97.8 | 98.1 | 95.6 | 99.1 | 97.8 | 98.8 | 70.5 |
| Conv. | | | | | | | | | | | | |
| PMS (Cp) | — | 79.0 | 72.4 | 78.1 | 87.4 | 97.3 | 97.8 | 94.0 | 98.6 | 96.2 | 97.8 | 37.2 |
| MMS (Cm) | — | 16.3 | 13.2 | 10.5 | 13.7 | 29.3 | 30.6 | 22.0 | 11.5 | −1.8 | −2.9 | 12.6 |
| Cp/Cm | — | 4.8 | 5.5 | 7.4 | 6.4 | 3.3 | 3.2 | 4.3 | 8.6 | — | — | 3.0 |

(1) Crystal size 0.2–0.5 microns

TABLE III-continued

| | EXAMPLE 9, calcined Na, Pt-ZSM-5 | | | | | |
|---|---|---|---|---|---|---|
| Run No. | 12 | 13 | 14 | 15 | 16 | 17 |
| Product Distribution (wt. %) | | | | | | |
| PET | 31.1 | 32.3 | 30.0 | 31.8 | 30.7 | 27.0 |
| MET | 13.9 | 6.0 | 2.9 | 2.9 | 2.1 | 0.7 |
| PMS | 0.5 | 1.2 | 5.3 | 1.4 | 3.8 | 8.5 |
| MMS | 53.7 | 59.7 | 60.8 | 61.8 | 62.9 | 63.3 |
| Others | 0.9 | 0.8 | 1.0 | 2.3 | 0.6 | 0.6 |
| % MS in Product | 54.1 | 60.9 | 66.1 | 63.1 | 66.6 | 71.7 |
| % para | 0.8 | 2.0 | 8.1 | 2.1 | 5.7 | 11.8 |
| % meta | 99.2 | 98.0 | 91.9 | 97.9 | 94.3 | 88.2 |
| % Conv. | | | | | | |
| PMS (Cp) | 98.6 | 96.7 | 85.5 | 96.2 | 89.6 | 76.8 |
| MMS (Cm) | 14.4 | 4.8 | 3.0 | 1.4 | 0 | 1.0 |
| Cp/Cm | 6.8 | 20.1 | 28.5 | 68.7 | — | 76.8 |

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. A process for obtaining m-methylstyrene from a mixture with p-methylstyrene that comprises hydrogenating a mixture of p-methylstyrene and m-methylstyrene in the presence of a modified zeolite having a Constraint Index of about 1 to about 12, a silica to alumina ratio of at least about 12, and a dried crystal density of not less than about 1.6 grams per cubic centimeter, modified with at least one element of Group IA, IIA, IVB, or VB of the Periodic Chart of the Elements and a metal of Group VIII of the Periodic Chart of the Elements; thereby obtaining a mixture of m-methylstyrene and p-ethyltoluene, and removing p-ethyltoluene by distillation.

2. The process of claim 1, wherein said mixture of p-methylstyrene and m-methylstyrene is vinyltoluene containing 50–70% meta isomer.

3. The process of claim 2, wherein the hydrogen feed rate is between about 0.05 and about 1.00 WHSV, the vinyltoluene feed rate is between about 0.1 and about 50 WHSV, and the temperature of hydrogenation is between about 150° C. and about 500° C.

4. The process of claim 3, wherein said modified zeolite is Na, Pt-ZSM-5.

5. The process of claim 3, wherein said modified zeolite is Na, Pd-ZSM-5.

6. The process of claim 3, wherein said modified zeolite is Na, Ni-ZSM-5.

7. The process of claim 3, wherein said modified zeolite is Na, Rh-ZSM-5.

8. The process of claim 3, wherein said modified zeolite is Pt, P-ZSM-5.

9. The process of claim 3, wherein said zeolite is ZSM-11.

* * * * *